(12) United States Patent
Mathis et al.

(10) Patent No.: US 9,578,883 B2
(45) Date of Patent: Feb. 28, 2017

(54) SILANE MODIFIED DIATOMACEOUS EARTH MECHANICAL INSECTICIDE

(71) Applicants: Jack L. Mathis, Conyers, GA (US); Sean G. Eubanks, Warner Robins, GA (US)

(72) Inventors: Jack L. Mathis, Conyers, GA (US); Sean G. Eubanks, Warner Robins, GA (US)

( * ) Notice: Subject to any disclaimer, the term of this patent is extended or adjusted under 35 U.S.C. 154(b) by 0 days.

(21) Appl. No.: 14/679,932

(22) Filed: Apr. 6, 2015

(65) Prior Publication Data

US 2015/0208660 A1   Jul. 30, 2015

Related U.S. Application Data

(62) Division of application No. 13/659,886, filed on Oct. 24, 2012, now Pat. No. 8,999,361.

(60) Provisional application No. 61/551,250, filed on Oct. 25, 2011.

(51) Int. Cl.

| | |
|---|---|
| *A01N 25/00* | (2006.01) |
| *A01N 55/00* | (2006.01) |
| *A01N 59/00* | (2006.01) |
| *A01N 65/00* | (2009.01) |

(52) U.S. Cl.
CPC ............. *A01N 55/00* (2013.01); *A01N 59/00* (2013.01); *A01N 65/00* (2013.01)

(58) Field of Classification Search
None
See application file for complete search history.

(56) References Cited

U.S. PATENT DOCUMENTS

| | | | |
|---|---|---|---|
| 2002/0141959 A1* | 10/2002 | Peterson ................ | A01N 55/00 424/70.12 |
| 2003/0077309 A1* | 4/2003 | Puterka .................. | A01N 25/26 424/411 |
| 2010/0298247 A1* | 11/2010 | Wilson .................. | A01N 43/22 514/28 |

* cited by examiner

*Primary Examiner* — Susan Tran
(74) *Attorney, Agent, or Firm* — Scott A. Hill; The Hill Law Firm, PLC

(57) ABSTRACT

A mechanical insecticide is made by mixing water with at least one type of silane to make a silane solution which is then mixed with uncalcined diatomaceous earth until there is substantial deposition of the silane material on the diatomaceous earth material, to make a silanized diatomaceous earth. The silanized diatomaceous earth can be diluted with water and applied to vertical and overhead surfaces using a sprayer, for the control of insects. The silanized diatomaceous earth can also be dried into a powder for broadcast application, or mixed as a paste for brush/roller/caulk application.

14 Claims, No Drawings

SILANE MODIFIED DIATOMACEOUS EARTH MECHANICAL INSECTICIDE

RELATED U.S. APPLICATION DATA

This application is a divisional of U.S. non-provisional application Ser. No. 13/659,886, filed on Oct. 24, 2012, which claimed the benefit of priority of U.S. provisional application No. 61/551,250, filed on Oct. 25, 2011, both titled "Silane Modified Diatomaceous Earth Mechanical Insecticide", both incorporated herein by reference in their entirety.

BACKGROUND OF THE INVENTION

Diatomaceous earth (DE) is a material predominately made up of the fossilized remains of diatoms, in particular the silica shell of diatoms known as a frustule, which are naturally occurring deposits characterized by lattice-like architectures. The physical structure of fossil diatoms includes numerous pores that give the material a very high surface pore volume and internal pore volume, contributing to the materials outstanding absorptive quality. DE is mined from sedimentary deposits and processed into a variety of grades useful in many applications. Such applications include filter material, abrasives, mechanical insecticide, cat litter, absorbents, chemical stabilizer (ex. nitroglycerin), and thermal insulator. Despite its many uses, there are constraints that limit the applicability of diatomaceous earth. For example, water borne applications are generally not practical. The material does not suspend in water or remain dispersed well enough for liquid spray application. Furthermore, prolonged storage in water results in compacted sediment that is difficult to re-suspend.

A well known use of DE is as a mechanical insecticide that kills numerous different crawling insects. It is generally accepted that when insects crawl over or through dry DE powder they will suffer physical damage to their waxy epicuticle, and then the absorptive quality of DE extracts lipids from the insects body, causing a lethal dehydration. Unfortunately, reliable application of DE to surfaces where insects often crawl can be difficult because DE does not easily suspend in water for spray applications, and application of dry powder DE does not allow for adequate coverage on vertical or overhead surfaces. DE is often applied by pressurized air, which creates nuisance dust. Unmodified DE has a high energy surface with numerous hydroxyl groups that hydrogen bond causing the material to become compact and claylike after settling in aqueous medium. There is a need for a DE that forms a suspension in water and has flow characteristics that make it amenable to spray application to all surfaces where insects cause problems.

SUMMARY OF THE INVENTION

The present invention relates to diatomaceous earth (DE) reacted with silanes. DE is modified by deposition of silanes to the DE substrate surface. Such modifications enhance or increase the functionality and applicability of DE because it can then be mixed with water and sprayed onto practically any surface. Silylated DE is produced by reacting with silanes of the formula $R_nSiX_{4-n}$, wherein n is equal to 0-3, R is an organic functional group, and X is a hydrolyzable group. Silanes are silicon chemicals that have a hydrolytically reactive center that can form stable covalent bonds with inorganic substrates. In addition, many silanes can polymerize, enhancing coverage of substrates. Furthermore silanes have an organic substitution that alters the properties of the substrate, making it suitable for a variety of physical interactions. Silylated DE, which has improved aqueous dispersion and suspension, can be used as an improved mechanical insecticide that can be applied by spraying a solution of silylated DE and water.

DETAILED DESCRIPTION OF THE INVENTION

The present invention is diatomaceous earth that has been modified when silanes form covalent bonds with the surface of diatomaceous earth and metal oxides naturally present in the material. It is the object of this disclosure to detail methods for modifying diatomaceous earth (DE) with silanes by deposition of one or more silanes or a combination of silanes. There are constraints of unmodified DE that can be overcome by modification with silanes such that the modified DE imparts novel and useful characteristics to the material.

This objective can be achieved by reacting the material with silanes of the formula $R_nSiX_{4-n}$, wherein n is equal to 0-3; preferably 0-2, more preferably, 1-2, most preferably 1, R is an organic functional group, and X is a hydrolyzable group. R groups can be methyl, linear alkyl, branched alkyl, aryl, etc. X can be hydrolysable groups such as chloro, alkoxy, amine/silazane, silanol, acetoxy, amine, dimethylamine, oxime, etc.

Silanes that alter the surface energy of a substrate without imparting chemical reactivity are referred to as non-functional silanes. Non-functional silanes fall into two classes, hydrophobic silanes and hydrophilic silanes. Hydrophobic non-functional silanes have organic substitutions such as; methyl, linear alkyl, branched alkyl, fluorinated alkyl, aryl, etc. Hydrophilic non-functional silanes have organic substitutions that are polar, hydroxylic, ionic, and charge inducible, etc.

Modification by non-functional silanes imparts a variety of useful properties to substrates. Such properties are hydrophobic, hydrophilic, lipophobic, lipophilic, oleophobic, oleophylic, charge conducting, ionic, release, etc. This has made silanized materials useful in a wide range of application such as; low energy coatings, pigment dispersants, water repellents, chromatography, conductive coatings, and antimicrobial coatings.

Excellent substrates for silanes include silica, quarts, glass, and stable metal oxides. These substrate have adequate hydroxyl groups (—OH) for deposition of silanes. Diatomaceous earth would likewise be a suitable substrate for silanization as it typically consists of 80-90% silica and roughly 5% stable metal oxides.

Moisture absorption and retention negatively impacts finer grades of DE used as insecticide. The cohesiveness of water causes DE particles to stick together in a fashion that alters the consistency of the material. As the material becomes coarser, fewer particles are able to attach to insects that crawl over or through the material.

Modification to diatomaceous earth can also be achieved by deposition of dipodal silanes of the formula $X_3Si$—$(CH_2)_n$—$R$—$(CH_2)$—$SiX_3$, wherein R is an organic functional group covalently bonded to both silyl groups, X is a hydrolyzable group. R groups can be alkyl, aryl, etc. X can be hydrolysable groups such as chloro, alkoxy, amine/silazane, silanol, acetoxy, amine, dimethylamine, oxime, etc.

Dipodal silanes are also useful for surface modification of diatomaceous earth. Dipodal silanes have the following chemical structure where X is a hydrolysable group and R is an organofunctional group:

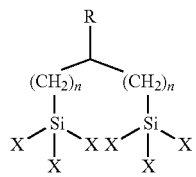

We have treated diatomaceous earth with a variety of silanes including organosilanes with organic substitutions that are hydrophobic, hydrophilic, and hydrophobic with embedded hydrophilicity. In general all varieties have shown some ability to improve diatomaceous earth as an insecticide. Thus far, of those we have tested, silanes with an organic substitution that can form hydrophobic phases with embedded hydrophylicity performed the best. This included 3-(trimethoxysilyl)propyldimethyl-octadecyl ammonium chloride; Hexadecyltrimethoxysilane, N,N-dioctyl-N'-triethoxysilyl proplylurea; and Trimethoxysilylpropyl-N,N,N-tri-n-butlyammonium bromide. Of particular value is the silane 3-(trimethoxysilyl)propyldimethyl-octadecyl ammonium chloride (also known as Octadecyldimethyl (3-trimethoxypropyl) ammonium chloride). It performed the best in insecticidal trial and also formulates the best in water, producing sprayable dispersions.

Applying Silanes—Methods of Deposition

The degree of silylation is dependent on the quantity of silane used in a particular reaction. Typically enough silane is added to assure monolayer deposition on the substrate; though less can be used for partial deposition and more for polylayer deposition. Polylayer deposition is also dependent on the type of silane. Silanes with three hydrolysable groups are most capable of polylayer deposition since, after initial deposition, they have free hydolyzable groups that can polymerize with silane monomers.

Estimates for silane loading on DE particles

| Particle Size | *Amount of Silane |
|---|---|
| <1 micron | 1.5% |
| 1-10 microns | 1.0% |
| 10-20 microns | 0.75% |
| >100 microns | 0.1% |

*minimum of monolayer coverage

Deposition from Aqueous Alcohol Solutions

Deposition of silane from aqueous alcohol solution is advantageous for producing dry DE products as volatile alcohols are easily removed by heat drying, evaporation, and/or vacuum. In addition, aqueous alcohol solution can dissolve water insoluble silanes.

The following method can be used for silylaton of diatomaceous earth: An aqueous alcohol solution is adjusted to pH 4.5-5.5 (typically with acetic acid). Silane is added to the solution and completely dissolved with stirring (silane concentration is dependant on the the particle size and amount of material to be silylated, in addition the volume of silylating solution has to be considered). Diatomaceous earth is added to the solution and mixed by stirring to assure even deposition on the substrate. Approximately ten minutes is allowed for silanol formation and deposition. The modified DE is cured by heating for 5-10 minutes at 110° C. or 24 hours at room temperature (<60% humidity). The material can be dried by low heat, evaporation or vacuum.

For the above procedure enough solution should be added to completely wet the substrate material, but excessive amounts are not necessary. In addition the solution should carry enough silane to attain the desired degree of deposition. Furthermore mixing speed should be adequate to prevent uneven deposition on the substrate.

Generally the following ranges can be used for preparing the aqueous alcohol solution to be used for silylation of DE. The ranges are in weight percent:

Formulation Range of Aqueous Alcohol Solution

| Ingredient | Operating Range | Preferred Range |
|---|---|---|
| Alcohol | 5-95 | 90-94.8 |
| Water | 5-95 | 5-9.8 |
| Acid | Quantity sufficient to adjust pH 4.5-5.5 | <0.1 |
| Silane | Quantity sufficient to achieve desired degree of deposition | 0.1-4.9 |

The following alcohols are preferred: ethyl, propyl and isopropyl. The following acids are preferred for adjusting pH: acetic.

Deposition from Aqueous Solution

Silane deposition from aqueous solution is preferred for producing liquid suspension, slurry, and gel of diatomaceous earth. Deposition from aqueous solution can be performed in the following manner: Silane is completely dissolved in water with mixing (the concentration used depends on the amount of substrate and degree of deposition, also the volume of water is considered). Insoluble silanes can be emulsified using nonionic surfactant. Diatomaceous earth is added with mixing. Mixing is continued for up to 10 minutes to assure even deposition on the substrate. Mild heating 40-70° C. for 10-30 minutes can accelerate deposition, however deposition at room temperature will occur.

Deposition Using Chlorosilanes in Anhydrous Alcohols

Example 1

Preparation of Silylated Diatomaceous Earth from Aqueous Solution

A 1000 gram (approximately 1 liter) solution was prepared in accordance with the present invention by mixing the following ingredients:

| Ingredient | Weight Percent (%) | Grams (g) |
|---|---|---|
| Water | 87.875 | 878.75 |
| Acid | 0.025 | 0.25 |
| 3-(trimethoxysilyl)propyldimethyl-octadecyl ammonium chloride | 0.1000 | 1.0 |
| DE | 12.000 | 120.0 |
| Totals | 100.000 | 1000.00 |

This formulation produces a suspension of 1-10 micron DE (unmodified) particles in aqueous medium. The particles will settle in the solution but remain loose and semidispersed. Untreated DE forms a sediment layer that becomes compact and will not suspend without vigorous and prolonged agitation.

Our invention remains dispersed and free flowing in the liquid phase and can be applied as a liquid spray. Modified DE is compatible with a variety of spray devices or technologies-trigger sprayers, pump sprayers, compressed liquid sprayers, electrostatic sprayers, airless sprayers, etc.

Research has shown an inversely proportional relationship between DE effectiveness and atmospheric humidity. Effectiveness decreases with increasing humidity. Atmospheric humidity could reduce the potential for insects to dehydrate, however; our research also indicates that atmospheric moisture negatively impacts DE. Absorbed moisture increases cohesion between particles due to hydrogen bonding between surface hydroxyl groups and water molecules. The effect of hydrogen bonding is to increase stiction (static friction) between particles. Stiction inhibits transfer of particles to insects that pass over or through diatomaceous earth.

Even without moisture there are still cohesive forces between particles of diatomaceous earth due to hydrogen bonding between surface hydroxyl groups of adjacent particles. Reducing the number of free hydroxyl groups would reduce the cohesive forces that affect transfer of DE particles to the surface of insects crawling over or through the material.

Needed is DE with fewer hydroxyl groups that create cohesive forces. Treatment with silanes reduces free hydroxyl groups. With fewer hydroxyl groups our invention is able to be formulated with water and is able to be applied as a mixture in the water phase. It recovers well after application in the aqueous phase and is more dry and powdery than unmodified DE. In addition by lowering static friction through quantitative reduction of free hydroxyl groups, it is better able to attach to insects that crawl over or through the material.

The invention, like traditional DE, can be used as a powder for broadcast application or mixing with grains, and there are several improvements over the current state of the art:

1. Silane modified DE is dispersable in water and can be formulated for liquid spray application.
2. Silane modified DE is more active and kills insects faster than natural or unmodified DE.
3. Silane modified DE resist negative impact of water whether absorbed after contact or from atmospheric humidity.
4. Silane modified DE is able to be used with natural and synthetic pyrethrins; and potentially is a better carrier of pyrethrins.
5. Because 3-(trimethoxysilyl)propyldimethyl-octadecyl ammonium chloride in an antimicrobial, silanes modified with it may also have antimicrobial properties. Grains, plants, fruits, vegetables and other perishables treated for insects may also be resistant to attack from bacteria and fungi.

Like natural unmodified DE, silane modified DE can potentially be considered inert as non-functional silanes of this invention are permanently bonded to the surface of DE.

The preferred silane of this invention, 3-(trimethoxysilyl) propyldimethyl-octadecyl ammonium chloride, consists of a relatively large lipophyllic hydrocarbon tail that would promote adsorption of the waxy cuticle that protects insects. In addition the cationic group of this same silane is hydrophilic and would promote adsorption of water and potentially accelerate dehydration of insects. We have treated DE with other organosilanes possess a hydrophobic substitution with embedded hydrophilicity that have also shown increased insecticidal rate. The invention is made by deposition of silane on the surface of diatomaceous earth. Three deposition reactions are preferable: 1) deposition from aqueous solution 2) deposition from aqueous-alcohol solution and 3) bulk deposition. Other known deposition reactions may be substituted, but may be less practical.

Deposition from aqueous solution is preferred for making solutions where the invention will remain in the liquid phase to be applied as liquid spray. Deposition from aqueous-alcohol solution is preferred for making dry material since volatile alcohols are easily removed by heat, evaporation, and vacuum distilation. Bulk deposition is also preferred for producing dry material.

For the invention, the degree of deposition ranges from 1 part silane to 50-2000 parts DE by weight (1:50-1:2000, silane:DE). Preferred for the invention is 1:100-500 silane:DE by weight.

Deposition form aqueous solution. Producing silane modified DE is a simple matter of adding DE to a silanating solution containing a quantity of silane sufficient to achieve the desired degree of deposition. Temperature and pH ranges are not given here. The optimum for pH is typically 4.0-5.0. Range of ingredients of the silane solution is as follows (figures are weight percent of total aqueous solution)

| Formulation range for aqueous silane solution (silanating silution). | | |
|---|---|---|
| Ingredient | Operating Range | Preferred Range |
| Water | 80.0-99.99 | 98.0-99.90 |
| Silane | 0.01-20.0 | 0.1-2.0 |

DE is added to the silane solution at the following ranges (in weight percent)

| Formulation range for making silane modified DE in aqueous solution | | |
|---|---|---|
| Ingredient | Range | Preferred Range |
| Silane Solution* | 50-99 | 65-99 |
| DE | 1-50 | 1-35 |

*The concentration of silane is dependent on the degree of deposition required

The above ranges produce viscous pastes or slurries to low viscosity aqueous dispersions or suspensions, which are suitable for direct application using a roller, brush, caulk gun or other application method commonly used for paints.

Deposition form aqueous alcohol solution. DE can be modified by mixing in an aqueous alcohol solution. The procedure requires preparation of an aqueous alcohol solution ranging from 10-95% alcohol, 95% preferred. Enough silane is added to give the desired degree of deposition. The table below gives formulation ranges for the silanating solution (ranges are expressed as weight percent). Temperature and pH ranges are not given here. The optimum for pH is typically 4.0-5.0.

| Formulation range for aqueous alcohol solution (silanating solution). | | |
|---|---|---|
| Ingredient | Operating Range | Preferred Range |
| Aqueous-alcohol solution* | 80.0-99.99 | 97.8-99.80 |
| Silane | 0.01-20.0 | 0.1-2.0 |

*Aqueous-alcohol solution range is 10-95% in water

DE is added to the silane solution at the following ranges (in weight percent)

| Formulation range for making silane modified DE using aqueous alcohol solution | | |
|---|---|---|
| Ingredient | Range | Preferred Range |
| Silane Solution* | 50-99 | 65-75 |
| DE | 1-50 | 25-35 |

*The concentration of silane is dependent on the degree of deposition required

After thorough mixing, alcohol can be removed by evaporation at room temperature or with heat. Alcohol can also be removed by vacuum distillation methods as well. Heating will help cure the silane layer.

Modification of DE by aqueous solutions produce pastes, slurries and dispersions (suspension) of the material. Paste and slurries can be used as they are or used as concentrates to make liquid dispersion. The liquid dispersions made by this method flow freely and are amenable to spray application. Even after settling the material can be re-suspended easily with light to moderate agitation.

Modified DE produced from reaction in aqueous medium can be dried and processed into powder if needed. If producing a dry product or powder, modified DE made using aqueous alcohol solution is more suitable as volatile alcohols are more easily removed by evaporation. DE modified with silanes from reaction in aqueous alcohol solution when rehydrated show characteristics similar to the material when made in aqueous solution.

Several types of silanes have shown the ability to modify DE with positive results. In particular the silane 3-(trimethoxysilyl)propyldimethyl-octadecyl ammonium chloride displays the best results for dispersion in water and for insecticidal activity.

Results of Insecticidal Trial:

Modified DE kills insect faster than unmodified DE of the same origin. The table below shows testing results. For the test below 10% liquid suspensions of DE were mixed with high agitation and quickly poured into Petri dishes. Excess DE was poured off and the material coating the Petri dishes was allowed to dry. After drying, beetles were placed in the dishes and monitored for kill time.

| Insecticidal Trial Results for Darkling Beetle | | | | |
|---|---|---|---|---|
| | | Modified[b] DE (weight ratio silane:DE) | | |
| DE Compositions: | [a]DE (unmodified) | 1:100 | 1:150 | 1:250 |
| Average Kill Time (hours): | 94 | 36 | 36 | 34 |

[a]natural diatomaceous earth, 10-50 micron particle size, average surface area 69 $m^2g^{-1}$
[b]modified with 3-(trimethoxysilyl)propyldimethyl-octadecyl ammonium chloride One obvious trait of silane modified DE was that more of it attaches to insects as they crawl over the material when compared to unmodified DE. This was true of all the types of silanes tested and hints that part of the insecticidal activity of silane modified DE is due to reduction of free hydroxyl groups on the surface of DE. Hydroxyl groups may cause cohesion that prevents DE particles from attaching to insects that crawl over it. Noteworthy is that silane modified DE is softer and more powdery whereas unmodified DE is more gritty and crystalline.

Other silanes were used to modify DE. These were chosen for having properties of hydrophobic or hydrophyllic or both. While they demonstrated increase insecticidal activity over unmodified DE they were not as effective as 3-(trimethoxysilyl)propyldimethyl-octadecyl ammonium chloride. They also were not as proficient at suspending DE particles in aqueous medium. They did however show an increase in particles attached to insects when tested as described above. This indicates that silane modification of DE in general increases insecticidal activity, possibly through reduction of free hydroxyl groups as described above.

While a preferred form of the invention has been shown and described, it will be realized that alterations and modifications may be made thereto without departing from the scope of the following claims.

What is claimed is:

1. A method for making a mechanical insecticide characterized by the steps of:
    mixing water with at least one type of silane to make a silane solution;
    mixing natural uncalcined diatomaceous earth having an average particle size greater than 20 microns with the silane solution, until there is substantial deposition of the silane material on the diatomaceous earth material, to make a silanized diatomaceous earth; and
    not adding a pest control agent to the mechanical insecticide.

2. The method of claim 1 further comprising the step of mixing the silanized diatomaceous earth with additional water to provide a fluid suspension; and wherein the step of applying the silanized diatomaceous earth is characterized by spraying the fluid suspension through a sprayer.

3. The method of claim 2 wherein the step of spraying is characterized by spraying the fluid onto vertical and overhead structures.

4. The method of claim 1 wherein the step of mixing water with at least one type of silane is further characterized by adding an alcohol to the mixture to make the silane solution.

5. The method of claim 4 further comprising the step of removing the alcohol from the silanized diatomaceous earth to produce a dry powder.

6. The method of claim 5 wherein the step of applying is characterized by broadcasting the dry powder.

7. The method of claim 1 wherein the ratio of silane to diatomaceous earth is in the range of 1:1 and 1:2000 by weight.

8. The method of claim 1 further comprising the step of adjusting the pH level of the silane solution to between 4.0 and 5.5.

9. The method of claim 8 wherein the step of adjusting the pH level is characterized by adding acetic acid.

10. The method of claim 1 further comprising the step of heating the silane solution to accelerate deposition on the diatomaceous earth.

11. The method of claim 1 wherein the type of silane is of the formula $R_nSiX_{4-n}$, wherein n is equal to 0-3, R is an organic functional group, and X is a hydrolyzable group.

12. The method of claim 1 wherein the type of silane is of the formula $X_3Si-(CH_2)_n-R-CH_2)-SiX_3$, wherein R is an organic functional group covalently bonded to both silyl groups, and X is a hydrolyzable group.

13. The method of claim 1 wherein the type of silane is 3-(trimethoxysilyl) propyldimethyl-octadecyl ammonium chloride.

14. The method of claim 1 wherein the amount of silane is adequate to assure monolayer deposition on the diatomaceous earth substrate.

* * * * *